United States Patent [19]

Gianino et al.

[11] Patent Number: 4,749,569

[45] Date of Patent: Jun. 7, 1988

[54] EXTRUDABLE ANTIPERSPIRANT COMPOSITION

[75] Inventors: Francis J. Gianino, Scituate; Philip P. Angelone, Jr., Wilmington, both of Mass.

[73] Assignee: The Gillette Company, Boston, Mass.

[21] Appl. No.: 935,598

[22] Filed: Nov. 28, 1986

Related U.S. Application Data

[63] Continuation of Ser. No. 720,815, Apr. 8, 1985, abandoned.

[51] Int. Cl.[4] .................. A61K 7/32; A61K 7/34; A61K 7/36; A61K 7/38
[52] U.S. Cl. .......................... 424/65; 424/66; 424/67; 424/68
[58] Field of Search .................. 424/65, 66, 67, 68

[56] References Cited

U.S. PATENT DOCUMENTS

| | | | |
|---|---|---|---|
| 4,425,321 | 1/1984 | Jacquet et al. | 424/68 |
| 4,477,431 | 10/1984 | Suffis et al. | 424/68 |
| 4,526,780 | 7/1985 | Marschner et al. | 424/66 |

FOREIGN PATENT DOCUMENTS

| | | | |
|---|---|---|---|
| 1119960 | 3/1982 | Canada | 424/68 |
| 0034609 | 4/1981 | Japan | 424/69 |
| 2018590 | 10/1979 | United Kingdom | 424/68 |
| 2096891 | 10/1982 | United Kingdom | 424/68 |

OTHER PUBLICATIONS

Cosmetics & Toiletries, 1/1982, vol. 97, pp. 71 and 72.

*Primary Examiner*—Dale R. Ore

[57] ABSTRACT

A stable extrudable antiperspirant paste composition exhibiting high antiperspirant efficacy in which finely divided solid astringent antiperspirant is dispersed in a limited class of volatile silicone liquid vehicles and stabilized against syneresis by a combination of finely divided silica and a quaternized three-layer clay exfoliated with a polar solvent.

14 Claims, No Drawings

EXTRUDABLE ANTIPERSPIRANT COMPOSITION

This is a continuation of application Ser. No. 720,815, filed Apr. 8, 1985, entitled Extrudable Antiperspirant Composition, now abandoned.

This invention relates to a stable extrudable antiperspirant paste composition exhibiting high antiperspirant efficacy and pertains more specifically to such a composition in which finely divided solid astringent antiperspirant is dispersed in a limited class of volatile silicone vehicles and stabilized against syneresis by a combination of finely divided silica and a quaternized three-layer clay exfoliated with a polar solvent.

It has previously been proposed to make antiperspirant compositions in which solid antiperspirant particles are suspended in volatile silicone liquids containing a mixture of silica and exfoliated clay, as described for example in UK No. 2,018,590A, UK No. 2,096,891A and Canadian patent No.1,119,960 but the art has generally failed to recognize the critical importance of employing silicones of defined characteristics and of excluding other commonly used ingredients in order to achieve a combination of high efficacy and freedom from syneresis after subjection to freeze-thaw cycling and/or prolonged storage. The development of novel applicators for antiperspirant compositions which require the composition to be in the form of a paste which is extrudable through restricted orifices has intensified the difficulty of combining high efficacy with stability in the form of freedom from syneresis in a single composition.

The present invention provides a stable extrudable antiperspirant paste composition consisting essentially of 4 to 25% by weight of finely divided solid astringent antiperspirant dispersed in 50 to 85% by weight of a vehicle consisting of liquid polydialkylsiloxane or liquid mixture of polydialkylsiloxanes in which each alkyl group has 1 to 3 carbon atoms and each molecule has 3 to 6 silicon atoms, a vapor pressure above 0.5 mm Hg at 35° C., a freezing point below −16° C., and a viscosity less than 10 centistokes at 25° C., and said vehicle including 0 to 10% of its weight of finely divided solid materials inert to the remaining ingredients of said composition; from 4.6 to 9.5% by weight of finely divided silica thickening agent; from 2 to 25% by weight of a guaternized three-layer clay exfoliated with and including a polar solvent from 0.03 to 6 times the weight of said clay; said composition being free from other hydrophobic liquids having a vapor pressure less than 50 mm Hg at 35° C. and being free from syneresis after storage for one month at temperatures up to 45° C. and after 10 freeze-thaw cycles.

There may be used in the composition of the present invention any of the generally known finely divided solid astringent antiperspirant active agents such as aluminum or zirconium salts or complexes or mixed aluminum-zirconium complexes, such as aluminum chlorohydrate, zirconyl hydroxychloride, complexes of aluminum chlorohydrate with zirconyl chloride and/or hydroxychloride with or without an amino acid buffer such as glycine, and the like. The amount of the antiperspirant active agent in the composition may vary from 4 to 25% by weight of the total composition but preferably is from 10 to 25%.

The properties and characteristics of the liquid vehicle present in the composition are of critical importance to achieve high efficacy and stability as evidenced by freedom from syneresis. The liquid vehicle must be a polydialkylsiloxane having 1 to 3 carbon atoms in each alkyl group and having from 3 to 6 silicon atoms per molecule or a mixture of such polydialkylsiloxanes; preferably the polydialkylsiloxane is cyclic. The polydimethylsiloxanes having 3 to 6 silicon atoms per molecule are preferred, particularly in cyclic form. It is essential that the liquid vehicle have a vapor pressure above 0.5 mm Hg at 35° C., a freezing point below −16° C. and a viscosity less than 10 centistokes at 25° C. Individual polydialkylsiloxanes of the class may be employed as the sole liquid provided they possess the reguisite additional characteristics set forth, but mixtures of two or more such polydialkylsiloxanes may be and preferably are employed provided the mixture exhibits the required characteristics even though one or more individual members of the mixture is lacking in one or more of the characteristics. Particularly preferred is a mixture of cyclic polydimethylsiloxane tetramer and pentamer in proportions from 1:9 to 5:9 by weight. Liquid vehicles of lower vapor pressures decrease the antiperspirant effectiveness of the composition and lead to staining of fabrics, e.g. clothing, which come into contact with the composition. Liquid vehicles of higher freezing point are unable to maintain the desired stability after repeated freeze-thaw cycling, and those having higher viscosity are unacceptable because they tend to give an oily somewhat greasy feel to the skin. The liquid vehicle must be present in an amount from 50 to 85% by weight of the total composition, preferably from 60 to 80% by weight for best results.

The finely divided silica functions as a thickening agent for the liquid vehicle and must be used within the range of 4.6 to 9.5%, preferably from 5 to 7.5% of the total composition. While colloidal or finely divided silica in any form can be used it is preferred to employ a mixture of hydrophilic and hydrophobic fumed silica. For best results it is preferred to employ a mixture having an average particle size of 10–20 nm. of hydrophobic with hydrophilic fumed silica in a ratio of 1:1 to 1:5 by weight. Hydrophilic fumed silica is made by high temperature flame hydrolysis of silicon tetrachloride and consists of amorphous particles of silica having silanol groups on their surface which are readily wetted with water. Hydrophobic fumed silica is made by reacting the hydrophilic material with an alkyl chlorosilane such as dimethyl dichlorosilane to convert most of the silanol groups to dialkyl siloxane groups; the material is not wetted with water.

It is also essential that the composition be free from other hydrophobic liquids or waxy solids which have vapor pressures less than 50 mm. Hg at 35° C. commonly employed as emollients or vehicles in antiperspirant compositions, such as mineral oil, esters or ethers, high molecular weight alcohols, and the like since their presence not only has an adverse effect upon the antiperspirant activity or efficacy of the composition but also causes staining of clothing or other fabrics coming into contact with the composition.

A quaternized three-layer clay exfoliated with a polar solvent in an amount from 0.03 to 6 times the weight of the clay is required to prevent syneresis and ensure stability of the composition. While any three-layer clay capable of being exfoliated or opened by mechanically shearing or heating in the presence of polar solvent can be used, quaternized montmorillonite such as quaternized bentonite or hectorite is the material of choice.

The clay preferably is opened by means of a polar solvent. The amount of such clay (including the polar solvent used) required to prevent syneresis ranges from 2 to 25% by weight of the total composition and is preferably from 2.5 to 12.5%. A variety of polar solvents can be used for exfoliating or opening the clay such as water, lower alcohols, propylene carbonate and the like, as is well known in the art. For optimum results there is used a mixture of ethyl alcohol (e.g. SD40) and deionized water in a ratio of 10:1 to 15:1 by weight.

There may be included in the composition of the present invention as described above, without affecting the basic and novel characteristics of the composition, such minor optional components as perfume or fragrance, antimicrobials, coloring agent, and, as a substitute for up to 10% by weight of the liquid vehicle, a finely divided solid material chemically inert to the remaining ingredients of the composition; among such materials are talc, titanium dioxide, oat flour, and hydrophobic corn starch such as aluminum starch octenylsuccinate sold under the name "Dry Flo".

In preparing the compositions of the present invention conventional mixing and shearing equipment can be employed; the mixing is most conveniently carried out at approximately room temperature although higher or lower temperatures can also be used. For ease of mixing, the quaternized clay is first mixed with the liquid vehicle, followed by the addition of the polar solvent and shearing to exfoliate the clay, after which the finely divided solid antiperspirant is stirred in with additional shearing, and finally the silica thickening agent is introduced with thorough agitation and shearing.

The composition of the present invention displays not only a high degree of antiperspirant efficacy when applied to the skin but also remarkable stability, remaining free from syneresis even after being subjected to repeated freeze-thaw cycles and/or to prolonged storage at room temperature and even at a temperature as high as 45° C. for a month or even longer.

The following specific examples are intended to illustrate more fully the nature of the invention without acting as a limitation upon its scope.

EXAMPLE 1

The following composition was prepared, in which the parts are by weight:

| | |
|---|---|
| Cyclic polydimethylsiloxane tetramer (SF 1173, General Electric) | 19.2 |
| Cyclic polydimethylsiloxane pentamer (SF 1202, General Electric) | 44.8 |
| Quaternized three-layer montmorillonite (Tixogel VP) | 3.5 |
| Ethyl alcohol, SD40 | 2.3 |
| Deionized Water | 0.2 |
| Aluminum zirconium tetrachlorohydroxide glycine | 23.5 |
| Hydrophobic fumed silica (Aerosil R-972, Degussa) | 2.4 |
| Hydrophilic fumed silica (Aerosil 200, Degussa) | 4.1 |

The ingredients were mixed together in the order listed at room temperature (20°-25° C.). The product was in the form of a paste which could readily be extruded through an orifice 1/16 inch in diameter or larger. It displayed no syneresis after storage at either room temperature or at 45° C. for one month. A specimen subjected to 10 freeze-thaw cycles (22° to −16° C.) also displayed no syneresis either immediately following the cycling or after further storage for one day at 22° C.

When tested for antiperspirant effectiveness by an absolute thermal sweat-reduction protocol, the product exhibited an effectiveness of over 50% sweat reduction.

Examples 2–11

The following compositions were prepared, in which the parts are by weight, using essentially the same procedure as in Example 1:

| Ingredient | 2 | 3 | 4 | 5 | 6 | 7 | 8 | 9 | 10 | 11 |
|---|---|---|---|---|---|---|---|---|---|---|
| Cyclic polydimethylsiloxane tetramer (DC-244 Fluid, Dow Corning) | 19.2% | 18.9% | — | — | 19.2% | 16.2% | — | — | — | — |
| Cyclic polydimethylsiloxane pentamer (DC-245 Fluid, Dow Corning) | 44.8 | 44.1 | — | — | 44.8 | 37.80 | — | — | — | — |
| Cyclic polydimethylsiloxane tetramer (SF 1173, G.E.) | — | — | 18.87 | 18.75 | — | — | 19.05 | 16.2 | 19.20 | 19.20 |
| Cyclic polydimethylsiloxane pentamer (SF 1202, G.E.) | — | — | 44.03 | 43.75 | — | — | 44.45 | 37.8 | 44.80 | 44.80 |
| Quaternized three-layer montmorillonite (Tixogel VP) | 3.5 | 3.5 | 3.5% | 3.50% | 3.50 | 3.50 | 3.50 | 3.50 | 3.50 | 3.50 |
| Ethyl alcohol, SD 40 | 2.31 | 2.31 | 2.31 | 3.70 | 2.31 | 2.31 | 2.31 | 2.31 | — | — |
| Propylene carbonate | — | — | — | — | — | — | — | — | 2.50 | — |
| Isopropyl alcohol | — | — | — | — | — | — | — | — | — | 2.31 |
| Deionized water | 0.19 | 0.19 | 0.19 | .30 | .19 | .19 | .19 | .19 | — | 0.19 |
| 5/6 Basic aluminum chlorohydrate | 23.50 | — | — | — | — | — | — | — | — | — |
| Aluminum chlorohydrate-zirconyl hydroxy chloride complex | — | 23.50 | 24.6 | 23.50 | 23.50 | 23.50 | 23.50 | 23.50 | 23.50 | 23.50 |
| Hydrophobic fumed silica (Aerosil R-972) | 2.42 | 2.79 | 2.42 | 2.42 | 1.62 | 2.42 | 2.42 | 2.42 | 2.42 | 2.42 |
| Hydrophobic fumed silica (Aerosil 200) | 4.08 | 4.71 | 4.08 | 4.08 | 4.88 | 4.08 | 4.08 | 4.08 | 4.08 | 4.08 |
| Perfume | — | — | — | — | — | — | 0.50 | — | — | — |
| Hydrophobic corn starch | — | — | — | — | — | 10.0 | — | — | — | — |
| Talc | — | — | — | — | — | — | — | 10.0 | — | — |

Each of the compositions of Examples 2–11 exhibited superior characteristics and properties similar to those of Example 1, and all were suitable for use as antiperspirants.

What is claimed is:

1. In an antiperspirant paste composition consisting essentially of 4 to 25% by weight of finely divided solid astringent active agent from 2 to 25% by weight of a quaternized three-layer clay exfoliated with and including polar solvent from 0.03 to 6 times the weight of said clay, wherein the improvement comprises from 4.6 to 9.5% by weight of finely divided silica thickening agent, and 50 to 85% by weight of a vehicle consisting of liquid polydialkylsiloxane or liquid mixture of polydialkylsiloxanes in which each alkyl group has 1 to 3 carbon atoms and each molecule has 3 to 6 silicon atoms, a vapor pressure above 0.5 mm Hg at 35° C., a freezing point below −16° C., and a viscosity less than 10 centistokes at 25° C., and said vehicle including 0 to 10% of its weight of finely divided solid materials inert to the remaining ingredients of said composition, being extrudable and free from other hydrophobic liquids having a vapor pressure less than 50 mm Hg at 35° C., said composition being free from syneresis after storage for one month at temperature up to 45° C. and after 10 freeze-thaw cycles.

2. An antiperspirant paste composition as claimed in claim 1 in which each alkyl group is methyl and in which said silica is a mixture of hydrophobic and hydrophilic fumed silica in a ratio of 1:1 to 1:5 by weight.

3. An antiperspirant paste composition as claimed in claims 1 or 2 in which said siloxanes are polydimethylcyclic siloxanes.

4. An antiperspirant paste composition as claimed in claim 1 or 2 in which said clay is a quaternized montmorillonite clay and said polar solvent is aqueous ethyl alcohol.

5. An antiperspirant paste composition as claimed in claim 1 or 2 in which the amount of said astringent antiperspirant is from 10 to 25% by weight, the amount of said liquid vehicle is from 60 to 80% by weight, the amount of said silica is from 5 to 7.5% by weight, the amount of said clay is from 2.5 to 12.5% by weight, and said composition is free from other finely divided solid materials.

6. An antiperspirant paste composition as claimed in claim 2 in which said clay is a quaternized montmorillonite clay and said polar solvent is aqueous ethyl alcohol and in which the amount of said astringent antiperspirant if from 10 to 25% by weight, the amount of said liquid vehicle is from 60 to 80% by weight, tha amount of said silica is from 5 to 7.5% by weight, the amount of said clay is from 2.5 to 12.5% by weight, and said composition is free from other finely divided solid materials.

7. An antiperspirant paste composition as claimed in claim 2 in which said siloxanes are polydimethylcylic siloxanes and said clay is a quaternized montmorillonite clay and said polar solvent is aqueous ethyl alcohol.

8. An antiperspirant paste composition as claimed in claim 7 in which the amount of said astringent antiperspirant is from 10 to 25% by weight, the amount of said liquid vehicle is from 60 to 80% by weight, the amount of said silica is from 5 to 7.5% by weight, the amount of said clay is from 2.5 to 12.5% by weight, and said composition is free from other finely divided solid materials.

9. An antiperspirant paste composition as claimed in claims 1 or 2 in which said liquid mixture of polydialkylsiloxanes is a mixture of cylic polydimethylsiloxane tetramer and pentamer in proportions from 1:9 to 5:9 by weight.

10. An antiperspirant paste composition as claimed in claim 6 in which said liquid mixture of polydialkylsiloxanes is a mixture of cylic polydimethylsiloxane tetramer and pentamer in proportions from 1:9 to 5:9 by weight.

11. An antiperspirant paste composition as claimed in claim 7 in which said liquid mixture of polydialkylsiloxanes is a mixture of cylic polydimethylsiloxane tetramer and pentamer in proportions from 1:9 to 5:9 by weight.

12. An antiperspirant paste composition as claimed in claim 8 in which said liquid mixture of polydialkylsiloxanes is a mixture of cylic polydimethylsiloxane tetramer and pentamer in proportions from 1:9 to 5:9 by weight.

13. An antiperspirant paste composition as claimed in claim 9 in which said vehicle includes 0 to 10% by weight of finely-divided solid material selected from the group consisting of talc, titanium dioxide, oat flour, and hydrophobic corn starch.

14. An antiperspirant paste composition as claimed in claim 12 in which said vehicle includes 0 to 10% by weight of finely-divided solid material selected from the group consisting of talc, titanium dioxide, oat flour, and hydrophobic corn starch.

* * * * *

UNITED STATES PATENT AND TRADEMARK OFFICE
CERTIFICATE OF CORRECTION

PATENT NO. : 4,749,569
DATED : JUNE 7, 1988
INVENTOR(S) : Francis J. Gianino et al.

It is certified that error appears in the above-identified patent and that said Letters Patent are hereby corrected as shown below:

Col. 1, line 48, "guaternized" should be --quaternized--;

Col. 2, line 14, "reguisite" should be --requisite--;

Col. 3, line 48 of the Example, "Hydrophobic fumed silica" (second occurrence) should be --Hydrophilic fumed silica--.

Signed and Sealed this

Twenty-fifth Day of October, 1988

Attest:

DONALD J. QUIGG

Attesting Officer

Commissioner of Patents and Trademarks